(12) United States Patent
Kawamura

(10) Patent No.: US 7,537,731 B2
(45) Date of Patent: May 26, 2009

(54) SPECIFIC BINDING ANALYSIS DEVICE

(75) Inventor: Tatsurou Kawamura, Kyotanabe (JP)

(73) Assignee: Panasonic Corporation, Osaka (JP)

( * ) Notice: Subject to any disclaimer, the term of this patent is extended or adjusted under 35 U.S.C. 154(b) by 715 days.

(21) Appl. No.: 10/272,575

(22) Filed: Oct. 16, 2002

(65) Prior Publication Data

US 2003/0077673 A1 Apr. 24, 2003

(30) Foreign Application Priority Data

Oct. 19, 2001 (JP) ............................. 2001-322447

(51) Int. Cl.
*G01N 33/48* (2006.01)

(52) U.S. Cl. .................................... 422/68.1

(58) Field of Classification Search ................ 422/105, 422/55, 56, 58, 104; 435/287.7, 287.8, 288.3
See application file for complete search history.

(56) References Cited

U.S. PATENT DOCUMENTS

| | | | |
|---|---|---|---|
| 4,094,647 A | 6/1978 | Deutsch et al. | |
| 4,321,057 A | 3/1982 | Buckles | |
| 4,366,241 A | 12/1982 | Tom et al. | |
| 4,426,451 A | 1/1984 | Columbus | |
| 4,435,504 A | 3/1984 | Zuk et al. | |
| 4,756,884 A | 7/1988 | Hillman et al. | |
| 4,857,453 A | 8/1989 | Ullman et al. | |
| 4,883,760 A | 11/1989 | Heelies | |
| 4,963,498 A * | 10/1990 | Hillman et al. ............... 436/69 |
| 5,073,216 A * | 12/1991 | Siegel et al. ............... 156/73.3 |
| 5,198,289 A | 3/1993 | Siegel et al. | |
| 5,200,321 A | 4/1993 | Kidwell | |
| 5,399,316 A | 3/1995 | Yamada | |
| 5,624,809 A | 4/1997 | Skold et al. | |
| 5,624,850 A | 4/1997 | Kumar et al. | |
| 5,976,896 A | 11/1999 | Kumar et al. | |
| 5,985,675 A | 11/1999 | Charm et al. | |
| RE37,437 E | 11/2001 | Friesen et al. | |
| 6,409,976 B1 | 6/2002 | Poschmann et al. | |
| 6,416,642 B1 | 7/2002 | Alajoki et al. | |
| 6,660,517 B1 * | 12/2003 | Wilding et al. ............ 435/289.1 |
| 6,663,833 B1 | 12/2003 | Stave et al. | |
| 6,767,710 B2 * | 7/2004 | DiNello et al. ................ 435/7.1 |

FOREIGN PATENT DOCUMENTS

| | | |
|---|---|---|
| EP | 0 310 862 A2 | 4/1989 |
| EP | 0 401 913 A1 | 12/1990 |
| JP | 07-055808 A | 3/1995 |
| JP | 07-167786 A | 7/1995 |
| JP | 08-240591 A | 9/1996 |
| JP | 10-073592 A | 3/1998 |
| WO | WO 89/06792 A1 | 7/1989 |

OTHER PUBLICATIONS

Erickson et al., Numerical Simulations of Capillary-Driven Flows in Nonuniform Cross-Sectional Capillaries, *Journal of Colloid and Interface Science*, 250, 422-430 (May 2002).

* cited by examiner

*Primary Examiner*—Terry A. McKelvey
*Assistant Examiner*—Deborah A. Davis
(74) *Attorney, Agent, or Firm*—Panitch Schwarze Belisario & Nadel LLP

(57) ABSTRACT

Disclosed is a specific binding analysis method capable of controlling the amount of specific binding to freely setting the sensitivity, concentration range and the like in an analysis, and a device used therefor. In order to optimize the amount of specific binding, the specific binding analysis method and the device used therefor restrain the amount and velocity of a sample passing, by capillarity, through a detection zone, by controlling the dimensions, ventilation resistance, hydrophilicity and the like in the portion of the device where the sample passes through.

6 Claims, 3 Drawing Sheets

SPECIFIC BINDING ANALYSIS DEVICE

BACKGROUND OF THE INVENTION

The present invention relates to a specific binding analysis method for performing a qualitative or quantitative analysis of an analyte in a sample.

With the recent expansion of medical care in households and communities as well as increase of clinical examinations requiring high urgency, there is an increasing demand for the development of a specific binding analysis method which can be performed even by persons other than the experts of the clinical examination, in a rapid, simple and accurate manner.

Many methods are known as the conventional specific binding analyses, which include immunoassay utilizing an antigen-antibody reaction, receptor assay employing a receptor and nucleic acid probe assay employing the hybridization of complementary nucleic acid sequences. Because of their high specificity, these specific binding analysis methods are being frequently used in the clinical examinations and in many other fields.

More specific examples of the immunoassay include chromatography. In chromatography, a liquid sample is brought into contact with a matrix comprising, for example, a porous carrier or a fine particle-packed carrier in each of which a specific binding substance is insolubilized (immobilized). Then, the presence or absence of an analyte in the sample is analyzed by utilizing a phenomenon in which the liquid sample flows out along the matrix by permeating force caused by capillarity (see, e.g., Japanese Patent Nos. 2504923 and 2667793, Japanese Examined Patent Publication No. Hei 7-78503, Japanese Unexamined Patent Publication Nos. Hei 10-73592 and Hei 8-240591).

More specifically, a specific binding substance, which is labeled with a labeling material freely detectable by naked eyes or with an optical method, is specifically bound to an analyte. The specific binding substance specifically bound to the analyte is then bound to a binding material immobilized on the matrix. Finally, the presence or absence of the analyte in the sample is analyzed, according to the labeled amount of the specific binding substance insolubilized on the matrix.

The carrier comprising the matrix used for such chromatography has a large surface area where a great amount of a specific binding substance can be immobilized, so that the collision between reacting molecules, which may cause a specific binding reaction, occurs with a higher frequency as compared to the reaction in a liquid phase. Accordingly, the above-described chromatography is advantageous from the viewpoint of the measurement sensitivity and the measurement time.

In the conventional chromatography described above, it is necessary to employ, as a matrix material, a water absorbing material in which a liquid sample can develop and move by capillarity. Examples of the water absorbing material include a glass fiber filter paper, cellulose film, nitrocellulose film and nylon film, each of which is porous material having a pore size of approximately 1 to 50 μm.

Among them, nitrocellulose is superior, because it is capable of binding to a large amount of protein such as an antibody without being previously sensitized. Moreover, nitrocellulose is commercially available in various pore sizes, so that the use of nitrocellulose makes it is possible to select the flow rate of a sample.

However, the pore sizes and surface hydrophilicity of a matrix material as describe above, comprising a fibrous material, is difficult to be controlled with a high degree of reproducibility in manufacturing. The mean value and distribution of the pore size, as well as the surface hydrophilicity of the fibrous material, have a significant influence on a velocity at which a sample develops and move, that is, a flow rate of the sample. Since a time during which a specific binding reaction occurs greatly depends on the flow rate of the sample, a measured value fluctuates with a change in the flow rate.

In other words, a measured value is extremely sensitive to the properties of the matrix material, and therefore, the measurement accuracy depends on the manufacturing accuracy of the matrix material.

Moreover, it is difficult to improve the manufacturing accuracy of the matrix material to such an extent that a sufficient accuracy is ensured in a quantitative measurement. Accordingly, it has been required to perform the step of screening the matrix material, resulting in a problem of increased cost. Since the pore size range and manufacturing accuracy of the matrix material are limited, there is also a limitation on the range of the sample flow rates to be selected.

Therefore, it is an object of the present invention to provide a specific binding analysis method capable of readily controlling a wide range of the flow rates of a sample with high reproducibility, and a specific binding analysis device used therefor. According to the present invention, it is possible to increase the range of flow rates of a sample to be selected and to reproduce the flow rates with high accuracy in the manufacturing process, thereby providing a highly accurate specific binding analysis device at a low cost.

BRIEF SUMMARY OF THE INVENTION

In order to solve the foregoing problems, the present invention provides a specific binding analysis method for qualitatively or quantitatively analyzing an analyte in a sample, comprising the steps of:

providing a specific binding analysis device comprising: a sample application zone for applying a sample containing an analyte; a space forming zone which is connected to the sample application zone and capable of exhibiting capillarity; and a detection zone which is provided in the space forming zone and capable of detecting a signal attributed to a specific binding reaction;

applying the sample to the sample application zone to allow the sample to move, by capillarity, into the detection zone in the space forming zone to cause a specific binding reaction, thereby generating a signal attributed to the specific binding reaction, the signal being detected to perform a qualitative or quantitative analysis; and restraining a velocity at which the sample passes through the detection zone such that an intensity of the signal is substantially constant for samples having the same concentration, thereby controlling a time during which the specific binding reaction occurs.

Herein, if a liquid sample such as a solution containing an analyte passes through the space forming zone in too short a time by capillarity, the analyte passes through the detection zone without reliably participating in a specific binding reaction in the space forming zone. Therefore, the present invention, with the use of the method described below, restrains a velocity at which the sample passes through the detection zone such that an intensity of the signal is substantially constant for samples having the same concentration, thereby controlling a time during which the specific binding reaction occurs.

Specifically, it is preferable that the cross-sectional area and length of a portion of the space forming zone opened to an external atmosphere is controlled to restrain a velocity at which the sample passes through the detection zone, thereby controlling a time during which the specific binding reaction occurs.

It is also preferable that an air-permeable member is disposed in the space forming zone at a portion thereof opened to an external atmosphere to restrain a velocity at which the sample passes through the detection zone, thereby controlling a time during which the specific binding reaction occurs. Herein, the above-described velocity of the sample may also be restrained by controlling the dimension, such as the length, of the air-permeable member.

Further, it is preferable that a contact angle between the space forming zone and the sample (or the hydrophilicity or water-repellency of a contact surface between the space forming zone and the sample) is controlled to restrain a velocity at which the sample passes through the detection zone, thereby controlling a time during which the specific binding reaction occurs.

It is preferable that the hydrophilicity of a contact surface between the space forming zone and the sample is controlled by performing a treatment to provide hydrophilicity or water-repellency on the contact surface to restrain a velocity at which the sample passes through the detection zone, thereby controlling a time during which the specific binding reaction occurs.

In this case, it is preferable to perform the above-described treatment to provide hydrophilicity or water-repellency with the use of a blocking agent or a surfactant for preventing a nonspecific absorption in the space forming zone.

Further, it is preferable that a length between the sample application zone and the detection zone is controlled to restrain a velocity at which the sample passes through the detection zone, thereby controlling a time during which the specific binding reaction occurs.

Further, it is preferable that the above-described specific binding analysis method comprises the steps of:

(A) causing the analyte to bind to a first specific binding substance which is capable of specifically binding to the analyte and labeled with a detectable labeling material;

(B) causing the analyte to bind to a second specific binding substance which is capable of specifically binding to the analyte and substantially immobilized in the detection zone;

(C) measuring an intensity of a signal which is generated in the detection zone and attributed to the labeling material; and (D) performing a qualitative or quantitative analysis of the analyte in the sample based on the intensity of the signal measured in the step (C).

It is preferable that, in the step (B), the first specific binding substance is caused to bind, via the analyte, to the second specific binding substance.

It is also preferable that the first specific binding substance is retained on a contact surface between the sample application zone and the detection zone in the space forming zone, and the first specific binding substance becomes movable on the contact surface when humidified by application of the sample, thereby allowing the first specific binding substance to move to the detection zone.

It is preferable that the above-described signal is a coloration, fluorescence or luminescence.

It is also preferable that at least one of the first specific binding substance and the second specific binding substance is an antibody.

It is also preferable that the labeling material is a particle containing a metal sol, a dye sol or a fluorescent substance, or a colored latex particle.

The present invention also relates to a specific binding analysis device for performing a qualitative or quantitative analysis of an analyte contained in a sample, the device comprising:

a sample application zone for applying a sample containing an analyte;

a space forming zone which is connected to the sample application zone and capable of exhibiting capillarity;

a detection zone which is provided in the space forming zone and capable of detecting a signal attributed to a specific binding reaction; and a ventilation resistance controlling means for restraining a velocity at which the sample passes through the detection zone, wherein a sample applied to the sample application zone moves, by capillarity, to the detection zone in the space forming zone to cause a specific binding reaction and a signal attributed to the specific binding reaction is detected to perform a qualitative or quantitative analysis.

It is preferable that the ventilation resistance controlling means is a material having ventilation resistance disposed in the space forming zone at a portion thereof opened to an external atmosphere.

It is also preferable that the ventilation resistance material is an air-permeable member.

Further, it is preferable that the contact surface between the space forming zone and the sample has hydrophilicity.

It is preferable that the space forming zone comprises two flat plates and a spacer defining a space between the flat plates, the detection zone being disposed on at least one of the flat plates, and a signal attributed to the specific binding reaction is detected through the at least one of the flat plates.

It is also preferable that the detection zone is formed by fixing a matrix carrier having a large surface area on at least one of the flat plates and immobilizing a specific binding substance in the matrix carrier.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

In the following, embodiments of the present invention will be described in detail with reference to drawings.

Figure 1:
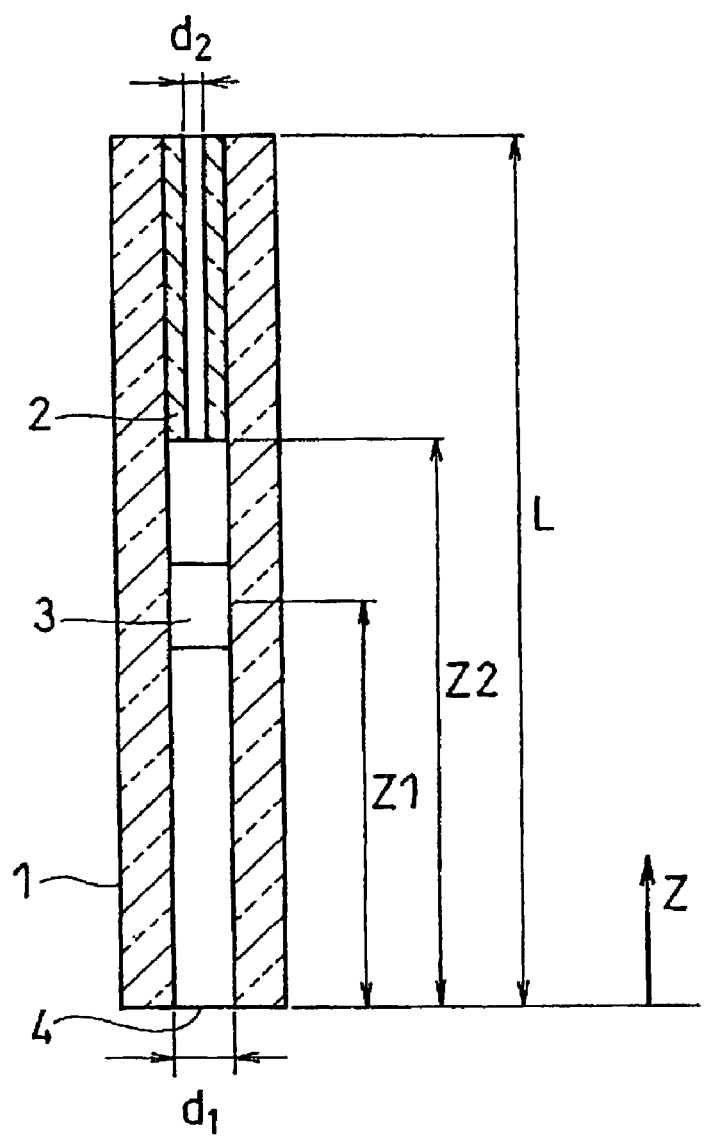
FIG. 1 is a schematic sectional view showing the structure of a specific binding analysis device of one embodiment in accordance with the present invention.
Figure 2:
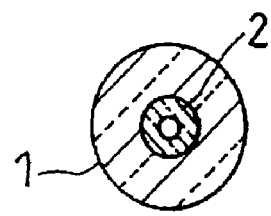
FIG. 2 is a schematic view of the specific binding analysis device shown in FIG. 1, taken from the Z direction.

FIG. 1 is a schematic sectional view showing the structure of a specific binding analysis device of one embodiment in accordance with the present invention. FIG. 2 is a schematic view of the specific binding analysis device shown in FIG. 1, taken from the Z direction.

The device comprises, for example, a glass capillary tube 1 having an inside diameter (d1) of 5 mm and a length (L) of 10 mm, which constitutes a space forming zone, and a glass capillary tube 2 having an inside diameter (d2) of 0.5 mm, a length (L) of 3 mm and an outside diameter of approximately 5 mm, which serves as a ventilation resistance controlling means.

As shown in FIG. 1, the glass capillary tube 2 is inserted in the glass capillary tube 1. Herein, the outer surface of the glass capillary tube 2 and the inner surface of the glass capillary tube 1 are in intimate contact with each other, so that substantially no air can permeate between the two capillary tubes. The glass capillary tube 2 and the glass capillary tube 1 are tightly bonded to each other, for example, by means of an adhesive.

Disposed inside the glass capillary tube 1 is a detection zone 3, which is formed by immobilizing a second specific binding substance as a binder on the inner wall of the glass capillary tube 1. The detection zone 3 is located at the distance (Z1) of approximately 2 mm from an opening 4 of the glass capillary tube 1 (the side where the glass capillary tube 2 is not inserted). Herein, "Z1" denotes the distance between the end of the opening 4 and the center of the detection zone 3. The distance (Z2) between the opening 4 of the glass capillary tube 1 and the opening of the glass capillary tube 2 in the glass capillary tube 1 is approximately 7 mm. In this embodiment, the opening 4 serves as a sample application zone.

After placing the specific binding analysis device shown in FIG. 1 such that the opening 4 faces downwards and the longitudinal direction of the device is substantially perpendicular to the horizontal direction, a liquid sample is brought into contact with the opening 4. As a result, the sample moves in the Z direction by capillarity. In other words, the liquid surface of the sample rises.

Herein, the liquid surface of the sample moves (rises) until the perpendicular component of the surface tension of the sample become equivalent to the gravity force exerted on the liquid column of the rising sample. When analysis was made on an aqueous solution such as urine as a sample at ordinary atmospheric pressure and room temperature using the device shown in FIG. 1, the amount of movement (moved distance) of the sample was approximately 6 mm. Herein, the liquid surface of the sample moved approximately 6 mm in about 30 seconds and thereafter became still.

In the case where the glass capillary tube 2 was absent, although the amount of movement of the sample was also approximately 6 mm, the velocity of movement thereof remarkably increased, so that the sample became still in two to three seconds. The reasons are as follows.

Since the sample pushes the air inside the glass capillary tube 1 while moving upwards by capillarity, the air also moves along with the sample. Herein, if the glass capillary tube 1 is completely sealed on the side thereof opposite from the opening 4, the air is compressed to increase the pressure inside the tube. Then, a difference between the pressure inside the tube and the atmospheric pressure, that is, the increased amount of pressure is further added to the gravity force, so that the sample becomes still after rising less than 6 mm.

On the other hand, if the glass capillary tube 1 is not completely sealed on the side thereof opposite from the opening 4, the air being compressed by the movement of the sample is gradually released outside the tube, so that the pressure inside the tube will eventually be equilibrium with the atmospheric pressure. Consequently, the sample rises 6 mm and thereafter becomes still. In this case, however, the time required for the sample to become still is increased, as compared to the case where the glass capillary tube 1 is completely opened to an external atmosphere on the side thereof opposite from the opening 4 (i.e. in the case where the glass capillary tube 2 is absent). In other words, the velocity of movement of the sample is decreased. The degree of decrease in the velocity of movement of the sample depends on the ventilation resistance of the glass capillary tube 1 on the side thereof opposite from the opening 4. Since the ventilation resistance varies depending on the presence or absence of the glass capillary tube 2, the velocity of movement of the sample also varies depending on the presence or absence of the glass capillary tube 2. Specifically, in the case where the glass capillary tube 2 is absent, the ventilation resistance is decreased to increase the velocity of movement of the sample, as compared to the case where the glass capillary tube 2 is present.

From the above, it is understood that the velocity of movement of the sample can be restrained by controlling the ventilation resistance of the glass capillary tube 1 on the side thereof opposite from the opening 4. Herein, the smaller the inside diameter (d2) of the glass capillary tube 2, i.e. the smaller the cross-sectional area of the internal space (space forming zone) and the longer the length of the glass capillary tube 2, the larger the ventilation resistance becomes. For example, when the glass capillary tube 2 had an inside diameter (d2) of 1.0 mm and a length (L) of 3 mm, the liquid surface of the sample rose 6 mm in 7 to 10 seconds and thereafter became still. On the other hand, when the glass capillary tube 2 had an inside diameter (d2) of 0.5 mm and a length (L) of 2 mm, the liquid surface of the sample rose 6 mm in 20 to 25 seconds and thereafter became still.

The above-described velocity of movement of the sample determines the time during which a specific binding reaction between the analyte and the second specific binding substance occurs in the detection zone 3. More specifically, a high velocity at which the sample passes through the detection zone 3 decreases the time during which the analyte in the sample passing through the detecting zone 3 interacts by collision with the second specific binding substance immobilized in the detection zone 3. Since the specific binding reaction is caused by the above-described interaction, the time during which a specific binding reaction occurs is also decreased, thereby decreasing the amount of the analyte bound by the specific binding reaction. That is to say that the amount of specific binding is decreased with an increase in the velocity of movement of the sample.

The reason is that, in the case of a capillary tube as shown in FIG. 1, the diffusion of the analyte in the longitudinal direction of the capillary tube (the Z direction) can be substantially ignored if an analysis is performed during a period of time as described in the present invention. In other words, under conditions as described above, the amount of specific binding substantially depends on the velocity of movement of the sample. This is, however, based on the assumption that the amount of the sample passing through the detection zone 3 is kept constant.

As described above, the velocity at which the sample passes through the detection zone 3 can be restrained by controlling the ventilation resistance of the glass capillary tube 1 on the side thereof opposite from the opening 4, thereby controlling the amount of specific binding. Consequently, a signal intensity can also be controlled, so that the sensitivity, concentration range and the like can be freely set in the analysis.

In addition, the capillary force acting on the sample moving in the capillary tube in the Z direction depends on the contact angle between the sample and the inner wall of the glass capillary tube 1, which constitutes the space forming zone. Herein, the contact angle of the sample on the inner wall of the glass capillary tube 1 is 0°.

The capillary force of the capillary tube varies according to the above-described contact angle, even between capillary tubes having space forming zones of identical dimensions, so that the amount and velocity of movement of the sample also vary according to the contact angle. Since the contact angle varies depending on the hydrophilicity (wetting properties (wettability) or ability to be wetted with an aqueous solution) of the inner wall of the capillary tube, the amount and velocity of movement of the sample can be restrained by controlling the hydrophilicity of the inner wall.

The hydrophilicity varies according to the material forming the inner wall of the space forming zone, and therefore can be controlled by selecting a material for forming the capillary tube. For example, the use of polystyrene or the like for forming the space forming zone results in a contact angle different from that obtained with the use of glass, thereby achieving amount and velocity of movement of the sample different from those obtained with the use of glass.

In addition, the inner wall which is to be brought into contact with the sample may be coated with a surfactant to change the hydrophilicity of the inner wall, thereby altering the contact angle, so that it becomes possible to restrain the amount and velocity of movement of the sample.

In a specific binding analysis, it is preferable to coat, with a blocking agent, the inner wall of the capillary tube other than a detection zone after immobilizing a specific binding substance in the detection zone, thereby reducing nonspecific absorption to the inner wall. The blocking may be performed by treating the inner wall with protein (e.g., bovine serum albumin or milk protein), polyvinylalcohol or ethanolamine, or a combination thereof. Additionally, skim milk may also be employed for this purpose. By selecting any one of these blocking agents or combining them, the contact angle can be readily changed, so that desired amount and velocity of movement of the sample can be achieved. This is effective in that the blocking can be performed while achieving the desired amount and velocity of movement of the sample at the same time.

The amount and velocity of movement of the sample can also be restrained by performing a plasma irradiation treatment on the inner wall to modify the hydrophilicity thereof.

As described above, the velocity and amount of the sample passing through the detection zone 3 can be restrained by controlling the contact angle between the inner wall of the glass capillary tube 1 and the sample, thereby controlling the amount of specific binding. Consequently, a signal intensity can also be controlled, so that the sensitivity, concentration range and the like can be freely set in the analysis.

The amount and velocity of movement of the sample can also be restrained by controlling the distance Z1 between the opening 4 and the detection zone 3. When the sample is rising by capillarity, a difference between the perpendicular component of the surface tension of the sample and the gravity force exerted on the liquid column of the rising sample is acting on the liquid surface of the sample. Accordingly, as the amount of the sample contained in the space forming zone increases with increasing height of the liquid surface, the difference acting on the liquid surface of the sample decreases. Finally, the velocity of movement becomes zero when the liquid surface reaches a predetermined height.

Therefore, the velocity at which the sample passes through the detection zone 3 can be restrained by controlling the distance Z1 between the opening 4 and the detection zone 3. More specifically, the amount and velocity of the sample passing through the detection zone 3 can be decreased by increasing the distance Z1, while it can be increased by decreasing the distance Z1.

As described above, the velocity and amount of the sample passing through the detection zone 3 can be restrained by controlling the distance Z1 between the opening 4 and the detection zone 3, thereby controlling the amount of specific binding. Consequently, a signal intensity can also be controlled, so that the sensitivity, concentration range and the like can be freely set in the analysis.

Figure 5:
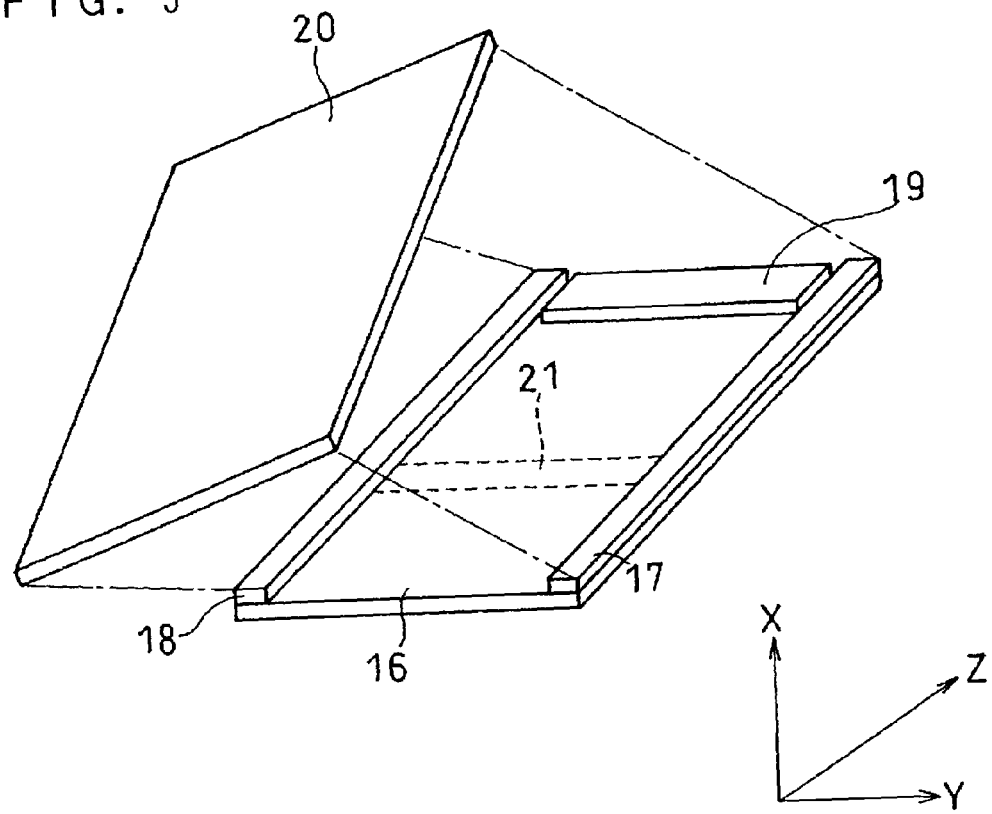
FIG. 5 is an exploded perspective view showing a specific binding analysis device of still another embodiment in accordance with the present invention.

Herein, FIG. 5 is an exploded perspective view showing the structure of a specific binding analysis device of another embodiment in accordance with the present invention. As shown in FIG. 5, the specific binding analysis device comprises: a substrate 16 made of glass or resin; spacers 17 and 18 each made of glass, resin, metal or the like, having a thickness (in the x direction) of approximately 250 µm; an air-permeable member 19 comprising the glass fiber filter paper GA-200 (manufactured by TOYO KABUSHIKI KAISHA), having a thickness (in the x direction) of approximately 250 µm; and a transparent substrate 20 made of glass or resin. Further, an anti-hCG monoclonal antibody capable of participating in a sandwich reaction with the hCG as a second specific binding substance is immobilized in the substrate 16 to form a detection zone 21.

Figure 6:
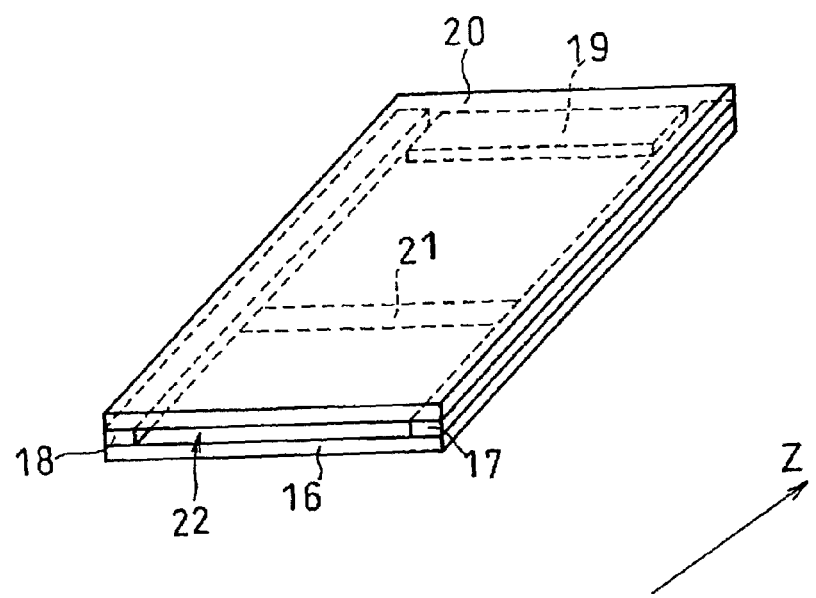
FIG. 6 is a partially see-through perspective view of the specific binding analysis device shown in FIG. 5 after assembly.

As shown in FIG. 6, the transparent substrate 20 and the substrate 16 are stacked, with the spacers 17 and 18 interposed therebetween. This gives a space forming zone constituted by the substrate 16, the spacers 17 and 18 and the transparent substrate 20, while forming a sample application zone 22, from which a sample can be introduced into the space forming zone.

Additionally, in the specific binding analysis device shown in FIGS. 5 and 6, the ventilation resistance can be controlled according to the thickness (in the x direction) of the spacers 17 and 18, the density of the glass fiber filter paper constituting the air-permeable member 19, the space (in the y direction) between the air-permeable member 19 and the spacers 17 and 18, the length (in the z direction) of the above-described space, and the like.

In the following, the present invention will be described in further detail by way of examples; however, the present invention is not limited thereto.

EXAMPLE 1 AND COMPARATIVE EXAMPLE 1

In this example, analysis was performed on human chorionic gonadotropin (hCG) in urine as an analyte, using the above-described specific binding analysis device shown in FIG. 1 in accordance with the present invention.

An anti-hCG monoclonal antibody capable of participating in a sandwich reaction with hCG was used both as a first specific binding substance and as a second specific binding substance, and colloidal gold was used as a labeling material. Herein, the use of colored particles of colloidal gold or the like allowed a labeled portion to be concentrated in a small zone or volume, because the colored particles were minute. This enabled an accurate qualitative and/or quantitative analysis of hCG to be performed in the detection zone 3, using a signal attributed to a reaction in which colloidal gold as the labeling material for the first specific binding substance participated. In addition, the inner wall of the glass capillary tube 1 was blocked by passing therethrough an aqueous dispersion of skim milk.

Firstly, a mixed solution of a colloidal gold-labeled anti-hCG monoclonal antibody and urine containing hCG as an analyte was prepared as a sample. Herein, the sample was in the state in which the analyte hCG was bound to the colloidal gold-labeled anti-hCG monoclonal antibody. When applied to the opening 4 serving as the sample application zone, the sample rose by capillarity, and the liquid surface (uppermost portion) of the sample moved approximately 5 mm in about 30 seconds and thereafter became still.

At this time, the analyte in the sample passing through the detection zone 3 specifically bound to the second specific binding substance. Accordingly, the analyte was immobilized, via the second specific binding substance, in the detection zone 3. In other words, the colloidal gold-labeled anti-hCG monoclonal antibody as the first specific binding substance bound, via the analyte hCG, to the anti-hCG monoclonal antibody as the second specific binding substance immobilized in the detection zone 3. Consequently, coloration occurred in the detection zone 3, according to the concentration of the analyte hCG.

Next, samples were prepared by adding hCG at various concentrations to control urines for accuracy control whose hCG concentrations were substantially zero. Then, the degree of coloration caused by colloidal gold in detection zone 3 was determined for each sample based on the above-described principle. The hCG concentrations of the samples were 0 (IU/L), 30 (IU/L), 100 (IU/L), 300 (IU/L), 1000 (IU/L), 3000 (IU/L) and 10000 (IU/L), respectively. As a result, it was confirmed that coloration occurred when using the samples having an hCG concentration of 300 (IU/L) or higher.

Next, the same analysis was performed except that the glass capillary tube 2 was not inserted in the glass capillary tube 1. In this case, the sample rose by capillarity, and the liquid surface thereof moved approximately 5 mm in about 2 to 3 seconds and thereafter became still. It was confirmed that coloration occurred only when using the sample having an hCG concentration of 10000 (IU/L).

As explained above, with the use of the specific binding analysis device of this embodiment, the velocity at which the sample passed through the detection zone 3 could be restrained by controlling the ventilation resistance of the glass capillary tube 1 on the side thereof opposite from the opening 4, thereby controlling the amount of specific binding. Consequently, a signal intensity could also be controlled, so that the sensitivity, concentration range and the like could be freely set in the analysis.

Additionally, although the colloidal gold-labeled first specific binding substance was mixed with urine prior to the application of the urine in this example, the first specific binding substance could also be retained, in the dry state, in a region between the opening 4 serving as the sample application zone and the detection zone 3. This allowed the urine to be directly applied to the opening 4 for analysis. In this case, the first specific binding substance retained in the dry state was able to migrate freely when wetted by the sample urine. Accordingly, the analyte and the first specific binding substance were allowed to move, while being bound to each other, to the detection zone 3, thereby causing coloration according to the concentration of the analyte.

EXAMPLE 2

Figure 3:
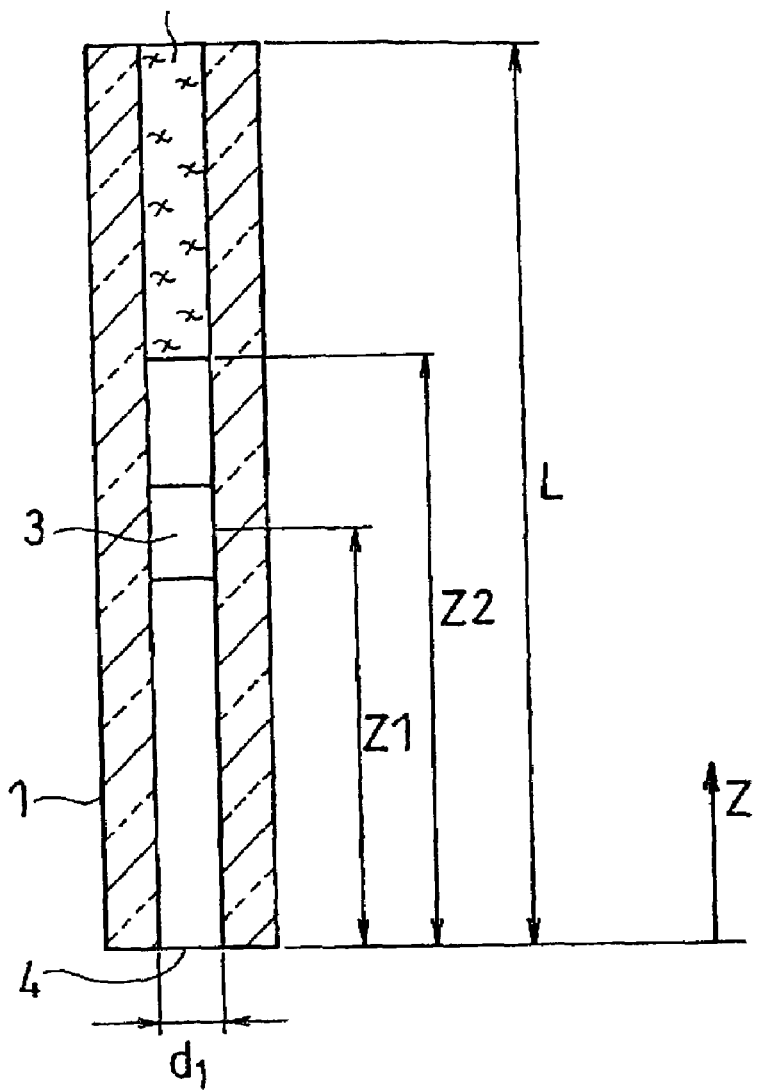
FIG. 3 is a schematic sectional view showing the structure of a specific binding analysis device of another embodiment in accordance with the present invention.

Next, analysis was performed on human chorionic gonadotropin (hCG) in urine as an analyte, using the specific binding analysis device shown in FIG. 3 in accordance with the present invention.

Figure 4:
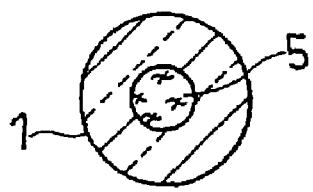
FIG. 4 is a schematic view of the specific binding analysis device shown in FIG. 3, taken from the Z direction.

In FIG. 3, the glass capillary tube 1, detection zone 3 and opening 4 serving as a sample application zone are the same as those in FIG. 1. Herein, however, a fibrous air-permeable member 5 was inserted in the glass capillary tube 1 on the side thereof opposite from the opening 4 to control the ventilation resistance of the glass capillary tube 1 on the side thereof opposite from the opening 4. In this example, the air-permeable member 5 was obtained by processing the glass fiber filter paper GA-200 (manufactured by TOYO KABUSHIKI KAISHA) into dimensions of a diameter of 0.5 mm and a length of 3 mm. Further, the inner wall of the glass capillary tube 1 was blocked with skim milk. FIG. 4 is a schematic view of the specific binding analysis device shown in FIG. 3, taken from the Z direction.

In this example, as in Example 1, a mixed solution of a colloidal gold-labeled anti-hCG monoclonal antibody and urine containing hCG as an analyte was prepared as a sample and the sample was applied to the opening 4. The sample rose by capillarity, and the liquid surface thereof moved 5 mm in about 120 seconds and thereafter became still.

Also as in Example 1, samples were prepared by adding hCG at various concentrations to control urines for accuracy control whose hCG concentrations were substantially zero. Then, the degree of coloration caused by colloidal gold in detection zone 3 was determined for each sample. The hCG concentrations of the samples were 0 (IU/L), 30 (IU/L), 100 (IU/L), 300 (IU/L), 1000 (IU/L), 3000 (IU/L) and 10000 (IU/L), respectively. As a result, it was confirmed that coloration occurred when using the samples having an hCG concentration of 100 (IU/L) or higher.

Further, the time required for the sample to rise inside the glass capillary tube 1 and thereafter became still, i.e. the velocity of movement of the sample could be varied by changing the length of the air-permeable member 5, thereby controlling the degree of coloration according to the concentration of the analyte.

As explained above, with the use of the specific binding analysis device of this example, the velocity at which the sample passed through the detection zone 3 could be restrained by controlling the ventilation resistance of the glass capillary tube 1 on the side thereof opposite from the opening 4 by means of the air-permeable member, thereby controlling the amount of specific binding. Consequently, a signal intensity could also be controlled, so that the sensitivity, concentration range and the like could be freely set in the analysis.

EXAMPLE 3

In this example, the same analysis as that of Example 2 was performed, except for the use of bovine serum albumin as a blocking agent in place of skim milk. As a result, the sample rose by capillarity, and the liquid surface thereof moved 4 mm in about 120 seconds and thereafter became still. It was confirmed that coloration occurred when using the samples having an hCG concentration of 300 (IU/L) or higher.

Further, the amount and velocity of movement of the sample could be varied by treating the inner wall of the glass capillary tube 1 with various surfactants, thereby controlling the degree of coloration in the detection zone according to the concentration of the analyte.

As explained above, with the use of the specific binding analysis device of this example, the velocity at which the sample passed through the detection zone 3 could be restrained by controlling the hydrophilicity of the inner wall of the glass capillary tube 1, thereby controlling the amount of specific binding. Consequently, a signal intensity could also be controlled, so that the sensitivity, concentration range and the like could be freely set in the analysis.

EXAMPLE 4

In this example, the same analysis as that of Example 1 was performed, using the same specific binding analysis device as that used in Example 1 except that the distance Z1 was 3 mm. As in Example 2, the sample rose by capillarity, and the liquid surface thereof moved 5 mm in about 120 seconds and thereafter became still. However, the amount and velocity of the sample passing through the detection zone 3 were different from those in Example 2, so that coloration properties different from those in Example 2 were observed in the detection zone 3.

As explained above, with the use of the specific binding analysis device of this example, the velocity and amount of the sample passing through the detection zone 3 could be restrained by controlling the distance Z1 between the opening 4 and the detection zone 3, thereby controlling the amount of specific binding. Consequently, a signal intensity could also be controlled, so that the sensitivity, concentration range and the like could be freely set in the analysis.

EXAMPLE 5

In this example, analysis was performed on human chorionic gonadotropin (hCG) in urine as an analyte, using the specific binding analysis device shown in FIGS. 5 and 6 in accordance with the present invention. An anti-hCG monoclonal antibody capable of participating in a sandwich reaction with hCG was used both as a first specific binding substance and as a second specific binding substance, and colloidal gold was used as a labeling material. Further, after the formation of the detection zone 21, the inner walls of the substrate 16 and the transparent substrate 20 were blocked by applying an aqueous dispersion of skim milk on the inner walls, followed by drying.

Firstly, a mixed solution of a colloidal gold-labeled anti-hCG monoclonal antibody and urine containing hCG as an analyte was prepared as a sample. Herein, the sample was in the state in which the analyte hCG was bound to the colloidal gold-labeled anti-hCG monoclonal antibody. After placing the specific binding analysis device such that the longitudinal direction (the z direction) of the device was substantially perpendicular to the horizontal direction, the sample was applied to a sample application zone 22 serving as an opening. After the application, the sample rose by capillarity to pass through the detection zone 21. Then, after an elapse of about two minutes, the sample became still before the liquid surface reached the air-permeable member 19.

In the detection zone 21, the analyte in the applied sample specifically bound to the second specific binding substance. As a result, the analyte was immobilized, via the second specific binding substance, in the detection zone 21. In other words, the colloidal gold-labeled anti-hCG monoclonal antibody as the first specific binding substance bound, via the analyte hCG, to the anti-hCG monoclonal antibody as the second specific binding substance immobilized in the detection zone 21. Consequently, coloration occurred in the detection zone 21. When the concentration of the analyte hCG was varied, coloration occurred according to the concentration. Further, it was confirmed that the coloration properties in the detection zone 21 could be controlled by changing the density of the air-permeable member 19.

As explained above, with the use of the specific binding analysis device of this embodiment, the velocity at which the sample passed through the detection zone 21 could be restrained by controlling the ventilation resistance of the space forming zone on the side thereof opposite from the sample application zone 22, thereby controlling the coloration properties in the detection zone 21. Additionally, in this example, the specific binding analysis device was readily produced since the detection zone 21 could be formed by stacking two flat plates.

EXAMPLE 6

In this example, the same analysis as that of Example 5 was performed, except that the detection zone 21 was formed by fixing glass fibers on the substrate 16 and further immobilizing, on the glass fibers or the like, an anti-hCG monoclonal antibody capable of participating a sandwich reaction with the hCG as the second specific binding substance, instead of by forming the detection zone 21 directly on the substrate 16.

In this example, the anti-hCG monoclonal antibody capable of participating in a sandwich reaction with the hCG as the second specific binding substance could be immobilized in the detection zone 21 in a greater amount than that in Example 5, so that the degree of coloration in the detection zone 21 could be increased.

As described above, with the use of the specific binding analysis method of the present invention and the device used therefor, the amount and velocity of a sample passing through a detection zone can be restrained to control the amount of specific binding, so that the sensitivity, concentration range and the like can be freely set in an analysis. That is to say that the present invention is extremely effective in practical applications.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

The invention claimed is:

1. A specific binding analysis device for performing a qualitative or quantitative analysis of an analyte contained in a sample, said device comprising:
   a first glass capillary tube having:
      first and second open ends,
      a first cavity that includes a detection zone in which a specific binding substance capable of binding an analyte is immobilized, and
      wherein said first open end serves as an opening portion for applying a sample containing said analyte; and
   a second glass capillary tube having:
      first and second open ends,
      a second cavity, and
      wherein said second glass capillary tube has a smaller cross-sectional area than said first glass capillary tube; and wherein said second glass capillary tube is inserted into said second end of said first glass capillary tube and an outer surface of said second glass capillary tube is hermetically bonded to an inner surface of said first glass capillary tube; and wherein said sample applied to said opening portion moves, by capillarity, to said detection zone in said first cavity to cause a specific binding reaction, and a signal attributed to said specific binding reaction is detected to perform a qualitative or quantitative analysis.

2. The specific binding analysis device of claim 1, wherein the first cavity has a uniform inside diameter.

3. The specific binding analysis device of claim 1, wherein the signal is a coloration, fluorescence, or luminescence.

4. The specific binding analysis device of claim 1, wherein the specific binding substance is an antibody.

5. The specific binding analysis device of claim 1, wherein a blocking agent for inhibiting absorption of the analyte onto the inner surface of the first capillary tube is applied to an area of the inner surface other than said detection zone.

6. A specific binding analysis device for performing a qualitative or quantitative analysis of an analyte contained in a sample, the device comprising:
- a first glass capillary tube of uniform inside diameter that includes:
  - a first end for receiving a sample,
  - a second end having an outside surface of a second glass capillary tube hermetically bonded to an inside surface of the first glass capillary tube, and
  - a detection zone having a binding substance immobilized on the inside surface of the first glass capillary tube and capable of binding to the analyte of said sample;
- wherein the sample applied to the first end of the first glass capillary tube moves by capillarity to the detection zone to cause a specific binding reaction, and wherein a signal attributed to the specific binding reaction is detected to perform a qualitative or quantitative analysis.

* * * * *